(12) United States Patent
Tagomori

(10) Patent No.: US 10,806,637 B2
(45) Date of Patent: Oct. 20, 2020

(54) ABSORBENT ARTICLE

(71) Applicant: DAIO PAPER CORPORATION, Ehime (JP)

(72) Inventor: Junta Tagomori, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 366 days.

(21) Appl. No.: 15/742,178

(22) PCT Filed: Jul. 22, 2016

(86) PCT No.: PCT/JP2016/071633
§ 371 (c)(1),
(2) Date: Jan. 5, 2018

(87) PCT Pub. No.: WO2017/022532
PCT Pub. Date: Feb. 9, 2017

(65) Prior Publication Data
US 2018/0193204 A1    Jul. 12, 2018

(30) Foreign Application Priority Data

Jul. 31, 2015  (JP) .................................. 2015-151811

(51) Int. Cl.
*A61F 13/15*      (2006.01)
*A61F 13/475*     (2006.01)
(Continued)

(52) U.S. Cl.
CPC ...... *A61F 13/4756* (2013.01); *A61F 13/4758* (2013.01); *A61F 13/533* (2013.01);
(Continued)

(58) Field of Classification Search
CPC .............. A61F 13/4756; A61F 13/4758; A61F 13/533; A61F 13/53409; A61F 2013/4587; A61F 2013/53409
(Continued)

(56) References Cited

U.S. PATENT DOCUMENTS 2,964,039 A * 12/1960 Johnson, Jr. ...... A61F 13/15804
                                                      604/366
3,736,931 A    6/1973 Glassman
(Continued)

FOREIGN PATENT DOCUMENTS

| JP | H11-189961 | 7/1999 |
| JP | 2008-173247 | 7/2008 |

(Continued)

OTHER PUBLICATIONS

International Search Report for PCT/JP2016/071633 dated Oct. 11, 2016.

*Primary Examiner* — Jacqueline F Stephens
(74) *Attorney, Agent, or Firm* — IPUSA, PLLC

(57) ABSTRACT

An absorbent article in which an absorbent body is provided between a liquid permeable topsheet and a backsheet, includes a concave groove-like or a slit-like absorbent body concave portion provided at a liquid permeable topsheet side of the absorbent body along a longitudinal direction of the absorbent article at an area including a urine expelling site, both end portions of the absorbent body concave portion in the longitudinal direction respectively being zones of a gradually decreasing width, each having a tapered shape whose width is gradually decreased toward an end portion side, each of the zones of a gradually decreasing width being formed to have a length that is greater than or equal to 20% of the total length of the absorbent body concave portion.

14 Claims, 14 Drawing Sheets

(51) Int. Cl.
*A61F 13/533* (2006.01)
*A61F 13/534* (2006.01)
*A61F 13/45* (2006.01)
*A61F 13/53* (2006.01)

(52) U.S. Cl.
CPC *A61F 13/53409* (2013.01); *A61F 2013/4587* (2013.01); *A61F 2013/530963* (2013.01)

(58) Field of Classification Search
USPC ............ 604/378, 379, 380, 385.01, 385.101
See application file for complete search history.

(56) References Cited

U.S. PATENT DOCUMENTS

| | | | | |
|---|---|---|---|---|
| 5,062,840 | A * | 11/1991 | Holt | A61F 13/495 604/385.19 |
| 6,245,962 | B1 * | 6/2001 | Muhs | A61F 13/15203 604/374 |
| 6,293,933 | B1 * | 9/2001 | Ahlstrand | A61F 13/49446 604/378 |
| 9,017,304 | B1 * | 4/2015 | Betts | A61F 13/47227 604/385.101 |
| 2003/0187416 | A1 * | 10/2003 | Shimoe | A61F 13/4704 604/379 |
| 2005/0148971 | A1 * | 7/2005 | Kuroda | A61F 13/512 604/380 |
| 2010/0057031 | A1 * | 3/2010 | Kuroda | A61F 13/4704 604/379 |
| 2012/0265162 | A1 | 10/2012 | Kuramochi | |
| 2014/0128828 | A1 | 5/2014 | Andersson et al. | |

FOREIGN PATENT DOCUMENTS

| | | |
|---|---|---|
| JP | 2009-056230 | 3/2009 |
| JP | 2010-194218 | 9/2010 |
| JP | 2011-130962 | 7/2011 |
| JP | 2012-090818 | 5/2012 |
| JP | 2014-518131 | 7/2014 |
| JP | 2014-171581 | 9/2014 |

* cited by examiner (FRONT SIDE)

(REAR SIDE)

(FRONT SIDE)

(REAR SIDE)

(FRONT SIDE)

(REAR SIDE)

(FRONT SIDE)

(REAR SIDE)

(FRONT SIDE)

(REAR SIDE)

(FRONT SIDE)

(REAR SIDE)

(FRONT SIDE)

(REAR SIDE)

(FRONT SIDE)

(REAR SIDE)

ABSORBENT ARTICLE

BACKGROUND OF THE INVENTION

1. Field of the Invention

The present invention relates to an absorbent article mainly used in incontinence pads, disposal diapers and the like.

2. Description of the Related Art

Conventionally, as absorbent articles mainly used in incontinence pads, disposal diapers and the like, a structure is known in which an absorbent body is provided between a liquid impermeable backsheet such as a polyethylene sheet or a non-woven-fabric made of laminated polyethylene sheets, and a liquid permeable topsheet such as a non-woven-fabric or a permeable plastic sheet.

In such absorbent articles, various structures in which a concave portion (concave groove) is formed at a skin side along a longitudinal direction are provided, as one of a temporarily reserving and urine diffusing means, for receiving a large amount of urine expelled at once at a small area and diffusing it rapidly, such as incontinence pads, for example.

For example, Patent Document 1 discloses a structure in which a concave portion that extends in a longitudinal direction of an absorbent article is integrally formed in a topsheet and in an absorbent layer. Patent Document 2 discloses a structure in which upper layer slits each penetrating from a front surface to a back surface of an upper layer absorbent body are formed at both lateral sides of a center line in a width direction in the upper layer absorbent body from a crotch portion to a rear side portion. Patent Document 3 discloses a structure in which a slit penetrating from a front surface side to a back surface side of an absorbent body is formed. The slit includes a first region that extends in a longitudinal direction of the absorbent body at least at a part of a center portion, and a second region in which both wall surfaces of the slit are formed to expand toward side edges of the absorbent body toward a front end portion side.

PATENT DOCUMENTS

[Patent Document 1] Japanese Patent No. 5105884
[Patent Document 2] Japanese Patent No. 5544100
[Patent Document 3] Japanese Patent No. 5578025

Here, urine that is introduced into a concave portion from a urine expelling site of a wearer is gradually absorbed in an absorbent body while flowing along the concave portion. Thus, an amount of the urine that flows in the concave portion decreases as moving away from the urine expelling site, and strength of urine current is lowered. In the structure described in Patent Document 1 or 2, the concave portion is formed along the longitudinal direction of the absorbent article with approximately the same width, and the urine may not reach both end portions because the strength of the urine current is lowered. Further, if the amount of the urine that flows in the concave portion is reduced with respect to the cross-sectional area of the concave portion, contact area between the urine and inner surfaces of the concave portion decreases, and there is a problem that absorption efficiency into the absorbent body is worsened, and absorption speed decreases.

Further, the slit described in Patent Document 3 is formed such that the both of the wall surfaces expand toward the side edges of the absorbent body toward the front end portion side of the absorbent body. Thus, the strength of the urine current is lowered due to the structure where the cross-section of the flow channel increases in addition to a reason that the amount of the urine that flows in the concave portion decreases as moving away from the urine expelling site. Thus, the urine is made more difficult to diffuse to the end portion side in this structure.

Further, when a wearer wears an absorbent article such as an incontinence pad, front and rear ends of the absorbent article respectively curve upward along the curves of a human body in front and rear directions of the human body (see FIG. 9). Thus, there is a problem that the urine cannot reach the front and rear ends due to influence of gravity at the upwardly curved front and rear ends. With this, the urine cannot be diffused to the entirety of the absorbent body.

SUMMARY OF THE INVENTION

The main purpose of the present invention is to provide an absorbent article having a structure in which urine can easily flow to front and rear end portions of a concave portion so that the urine can diffuse to the entirety of an absorbent body.

According to an embodiment, there is provided an absorbent article in which an absorbent body is provided between a liquid permeable topsheet and a backsheet, including a concave groove-like or a slit-like absorbent body concave portion provided at a liquid permeable topsheet side of the absorbent body along a longitudinal direction of the absorbent article at an area including a urine expelling site, both end portions of the absorbent body concave portion in the longitudinal direction respectively being zones of a gradually decreasing width, each having a tapered shape whose width is gradually decreased toward an end portion side, each of the zones of a gradually decreasing width being formed to have a length that is greater than or equal to 20% of the total length of the absorbent body concave portion.

BRIEF DESCRIPTION OF THE DRAWINGS

FIG. 100 is a plan view illustrating another example of the structure of the absorbent body concave portion of the embodiment;

DETAILED DESCRIPTION OF THE PREFERRED EMBODIMENTS

The invention will be described herein with reference to illustrative embodiments. Those skilled in the art will recognize that many alternative embodiments can be accomplished using the teachings of the present invention and that the invention is not limited to the embodiments illustrated for explanatory purposes.

Although an incontinence pad that absorbs expelling fluid such as urine is exemplified as an example of the absorbent article in the following embodiments, the absorbent article may be a disposal diaper (including a urine pad) that absorbs expelling fluid such as urine, a sanitary napkin that absorbs menstrual blood, a panty liner that absorbs vaginal discharge and the like.

(Basic Structure of Incontinence Pad 1)

Figure 1:
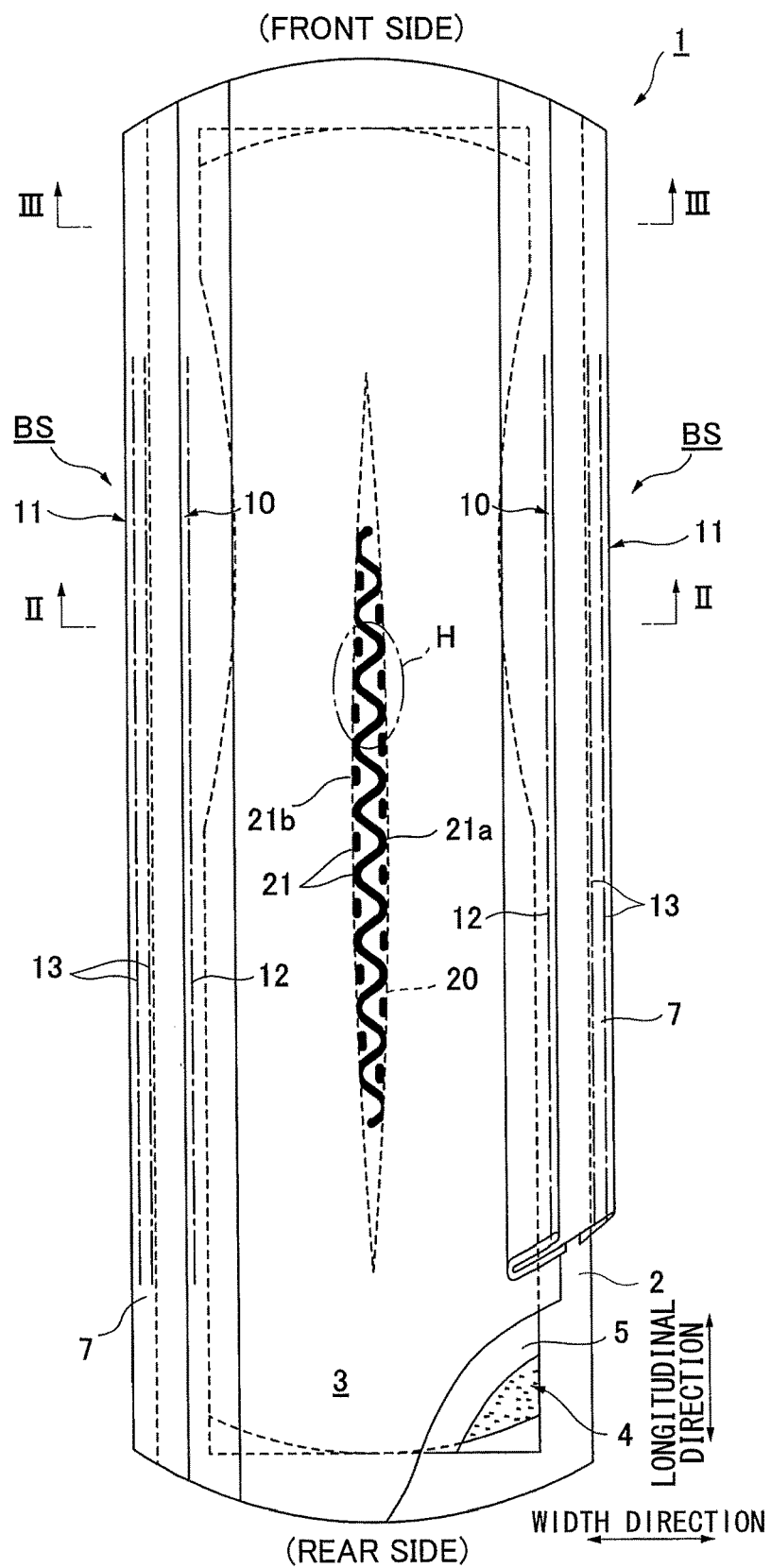
FIG. 1 is a partially cutaway development elevation view illustrating an example of an incontinence pad of an embodiment.
Figure 2:
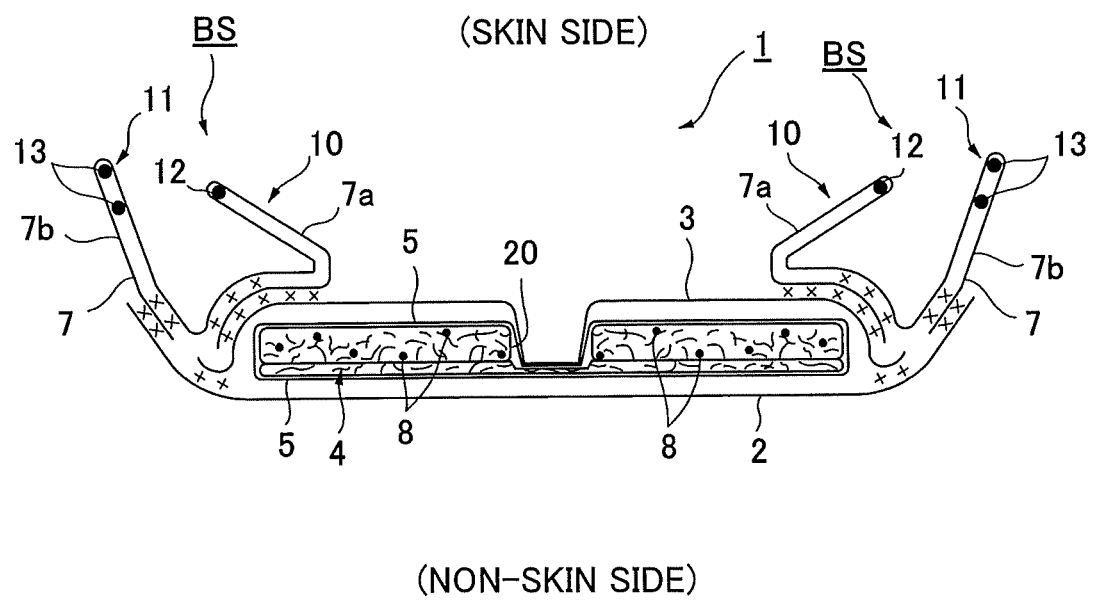
FIG. 2 is a cross-sectional view taken along line II-II of FIG. 1.
Figure 3:
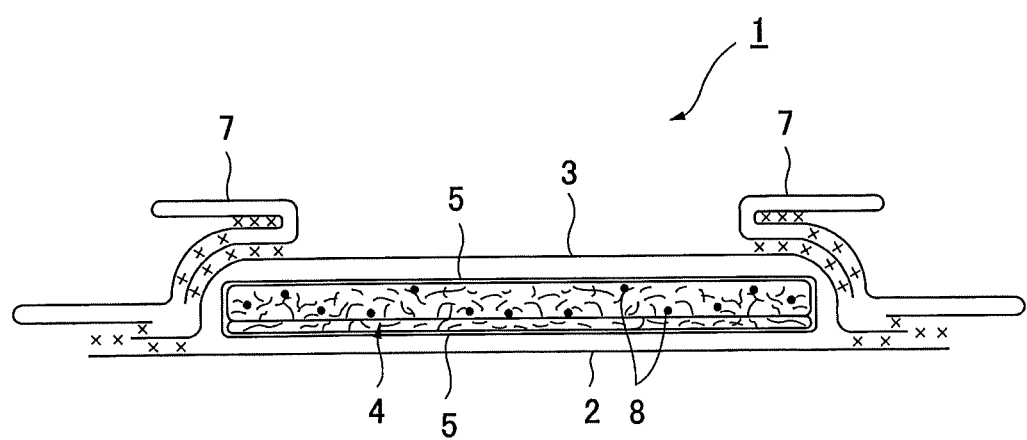
FIG. 3 is a cross-sectional view taken along line of FIG. 1.

FIG. 1 to FIG. 3 are views illustrating an example of a structure of an incontinence pad 1 of the embodiment. FIG. 1 is a partially cutaway development elevation view illustrating an example of the structure of the incontinence pad 1 of the embodiment. FIG. 2 is a cross-sectional view taken along, line II-II of FIG. 1. FIG. 3 is a cross-sectional view taken along line III-III of FIG. 1.

The incontinence pad 1 mainly includes a liquid impermeable backsheet 2, a liquid permeable topsheet 3, an absorbent body 4 provided between the liquid impermeable backsheet 2 and the liquid permeable topsheet 3, an encapsulating sheet 5 and side non-woven fabrics 7.

The liquid impermeable backsheet 2 is made of, for example, a polyethylene sheet or the like. The liquid permeable topsheet 3 may be configured to rapidly transmit urine or the like. The absorbent body 4 is made of, for example, cotton-like pulp, synthetic pulp or the like. The encapsulating sheet 5 is provided to surround the absorbent body 4 for retaining the shape and improving diffusibility of the absorbent body 4. The encapsulating sheet 5 is made of, for example, a crepe paper, a non-woven-fabric or the like. The side non-woven fabrics 7 form a lateral pair of standing gathers BS that protrude toward a skin side in a predetermined zone in a longitudinal direction including at least a urine expelling area H while standing from approximate side edge portions of the absorbent body 4. The urine expelling area H means an area corresponding to a site of a human body from which urine is expelled when a wearer wears the incontinence pad 1.

Further, at longitudinal end edge portions of the absorbent body 4, outer edge portions of the liquid impermeable backsheet 2 and the liquid permeable topsheet 3 are bonded by an adhesive such as a hot-melt adhesive or adhesive means such as a heat seal. Further, at both side edge portions of the absorbent body 4, the liquid impermeable backsheet 2 that extends further than the absorbent body 4 in a lateral direction and the side non-woven fabrics 7 are bonded by an adhesive such as a hot-melt adhesive or adhesive means such as a heat seal. Further, if necessary, a hydrophilic second sheet may be provided between the liquid permeable topsheet 3 and the absorbent body 4.

Next, each of the structures of the incontinence pad 1 is further described in detail.

As a material of the liquid impermeable backsheet 2, a sheet material having at least a water shielding property such as polyethylene or polypropylene may be used. Further, as another example, as a material of the liquid impermeable backsheet 2, a non-woven-fabric sheet or the like may be used while substantially ensuring impermeability by interposing a waterproof film. In such a case, the liquid impermeable backsheet is constituted by the waterproof film and the non-woven-fabric. Further, the liquid impermeable backsheet 2 may be configured to have moisture permeability as well in order to prevent sweating. As a seat material having a water shielding property and moisture permeability, a microporous sheet may be used that is obtained by forming a sheet by melting and kneading inorganic filler in olefin series resin such as polyethylene or polypropylene and then extruding the sheet in one axial direction or two axial directions.

As a material of the liquid permeable topsheet 3, a perforated or imperforate non-woven fabric or a porous plastic sheet may be used. As a material fiber for constituting the non-woven fabric, for example, a synthetic fiber including an olefin series such as polyethylene or polypropylene, a polyester series, a polyamide series and the like, a regenerated fiber such as rayon or cupra (cuprammonium rayon), a natural fiber such as cotton may be used. Such a non-woven-fabric may be formed by an appropriate processing method such as a spun lace method, a spun bond method, a thermal bond method, a melt blown method or a needle punch method. Among these processing methods, the spun lace method is superior in terms of great flexibility and drape properties, and the thermal bond method is superior in terms of bulkiness and softness.

The absorbent body 4 may be constituted by, for example, an absorbent fiber such as cotton-like pulp and a super absorbent polymer 8. In the illustrated example, the absorbent body 4 is formed in a substantially oval shape that is longer in the pad longitudinal direction. The super absorbent polymer 8 may be formed into granular powders, for example, and dispersedly mixed into the pulp constituting the absorbent body 4.

As the pulp, chemical pulp obtained from wood, a cellulose fiber such as dissolving pulp, and an artificial cellulose fiber such as rayon or acetate may be exemplified. Softwood pulp having a fiber length longer than that of hardwood pulp is preferably used in terms of function and price. The absorbent body 4 is surrounded by the encapsulating sheet 5 in the incontinence pad 1 of the embodiment. Thus, the encapsulating sheet 5 is provided between the liquid permeable topsheet 3 and the absorbent body 4. With this, the urine can be rapidly dispersed by the encapsulating sheet 5 having good absorbency, and flowback of the urine or the like can be prevented. The fabric weight per unit area of the pulp may be 100 g/m² to 600 g/m², and preferably, 200 g/m² to 500 g/m².

As a material of the super absorbent polymer 8, for example, a cross-linking polyacrylate, a self-cross-linking polyacrylate, a saponified substance of a cross-linking copolymer of acrylic acid ester and vinyl acetate, a cross-linking substance of a copolymer of isobutylene and maleic anhydride, a cross-linking polysulfonate, and a partially cross-linking substance of a water swellable polymer such as polyethylene oxide and polyacrylamide may be used. Among them, a substance of acryl acid or an acrylate series substance having a large amount of water absorption and a high absorption speed is preferable. The water-absorbency (water-absorbing ratio) and the water absorption speed of the super absorbent polymer 8 can be adjusted by adjusting the cross-linking density and the cross-linking density gradient in its manufacturing process.

Moreover, a synthetic fiber may be mixed into the absorbent body 4. The synthetic fiber may be, for example, a polyolefin series such as polyethylene or polypropylene, a polyester series such as polyethylene terephthalate or polybutylene terephthalate, and a polyamide series such as nylon, and a copolymer thereof, or a mixture of two kinds thereof. Further, a composite fiber such as a core-clad type fiber including a core made of a fiber with a high melting point and a clad made of a fiber with a low melting point, a side-by-side type fiber, and a division type, can be also used. When the synthetic fiber is made of a hydrophobic fiber, it is preferable to treat a surface of the synthetic fiber with a hydrophilic agent so as to have hydrophilic properties to the urine.

As the absorbent body 4, a polymer sheet may be used in which a super absorbent polymer is interposed between an upper layer sheet and a lower layer sheet respectively made of non-woven-fabrics or the like, instead of the above described structure in which the super absorbent polymer 8 is dispersedly mixed in the absorbent fiber. The polymer sheet may have a structure in which the upper layer sheet and the lower layer sheet are directly bonded at their outer edge portions by a hot-melt adhesive, a heat seal, ultrasonic sealing or the like, and the super absorbent polymer is encapsulated between the sheets. Further, the super absorbent polymer may be a structure in which the upper layer sheet and the lower layer sheet are bonded by a binder such as a hot-melt adhesive. The super absorbent polymer may not be provided or may be provided at a bottom portion of an absorbent body concave portion 20, which will be described later in detail.

In this embodiment, the absorbent body 4 may have a structure in which an arc-shape portion is cut-off at a predetermined zone in the longitudinal direction corresponding to the crotch portion. With this, hardness at the crotch portion for the wearer can be eliminated. Alternatively, the width of the absorbent body 4 may be substantially the same along the entire length.

As a material of the encapsulating sheet 5, a liquid permeable sheet such as a paper material such as a tissue, or a non-woven-fabric may be used. In particular, it is preferable to use the non-woven fabric for which damage (split) to a material hardly occurs. As such a non-woven-fabric, a non-woven-fabric processed by a spun bond method or an SMS method, a non-woven-fabric processed by a method by which a web is directly formed in a spinning process such as a spun bond method or a melt blow method from an elastic fiber made of thermoplastic elastomer resin or the like, or a non-woven fabric containing a material having elasticity such as latex, urethane, olefin series fiber as a main constituent is preferable as it has a good balance between thinness and strength. Here, for the encapsulating sheet 5, its hydrophilic degree is not specifically limited as long as a surface at a skin side surface (front surface side) of the absorbent body 4 is not water repellent.

On both side portions of the incontinence pad 1 at the skin side, the side non-woven fabrics 7 are provided along the longitudinal direction over the entire length of the incontinence pad 1. Outer portions of the side non-woven fabrics 7 laterally extend while the liquid impermeable backsheet 2 laterally extends. Side flaps in each of which the absorbent body 4 is not provided are formed at both side portions of the absorbent body 4 by bonding the laterally extended portions of the side non-woven fabrics 7 and the laterally extended portions of the liquid impermeable backsheet 2 by a hot-melt adhesive or the like.

As the side non-woven fabric 7, either water-repellent non-woven fabric or hydrophilic non-woven fabric may be used depending on the desired function. For example, when regarding a function of preventing urine or the like from permeating or of improving a texture as important, the water-repellent non-woven fabric such as SSMS, SMS or SMMS coated with water-repellent agent and the like of a silicon series, a paraffin series and an alkyl chromic chloride series may be used. On the other hand, when regarding the absorbability of the urine as important, the hydrophilic non-woven fabric obtained by making a swellable or porous synthetic fiber and then providing the hydrophilic property for the synthetic fiber by using capillary action. Such a hydrophilic non-woven fabric may be manufactured by a method of polymerizing the synthetic fiber in the presence of a compound having a hydrophilic group, for example, an oxidation product of polyethylene glycol, in the manufacture of the synthetic fiber, or a method of treating the surface with a metallic salt such as stannic chloride to partially dissolve the surface to form a porous surface and then to precipitate a metallic hydroxide on the surface. As the side non-woven fabric 7, a fiber obtained by processing the natural fiber, the synthetic fiber or the regenerated fiber by a proper processing method may be used.

In this embodiment, the side non-woven fabrics 7 form the standing gathers BS of a double gather structure including a lateral pair of inner standing gathers 10 and a lateral pair of outer standing gathers 11 that are positioned relatively outsides of the inner standing gathers 10, respectively. The inner standing gathers 10 are properly folded and stand from the neighborhood of the substantially side edges of the absorbent body 4 toward the skin side, respectively. The outer standing gathers 11 constitute the side flaps that laterally protrude from the absorbent body 4, respectively. The outer standing gathers 11 are constituted by the liquid impermeable backsheet 2 and the side non-woven fabrics 7 and stand toward the skin side, respectively.

The structure of the inner standing gathers 10 and the outer standing gathers 11 is described in detail with reference to FIG. 2 and FIG. 3. As illustrated in FIG. 2, double sheet parts 7a, 7b are respectively formed on the inner side and the outer side in the width direction by folding both sides of the side non-woven fabrics 7 in the width direction. One or a plurality of (one in the illustrated example) threadlike elastic stretchable members 12, each of which is fixed at both of the ends or at an appropriate position in the longitudinal direction, are provided in each of the laterally inner double sheet portions 7a. Further, one or a plurality of (two in the illustrated example) threadlike elastic stretchable members 13, each of which is fixed at both of the ends or at an appropriate position in the longitudinal direction, are provided in each of the laterally outer double sheet portions 7b. A base edge portion of each of the laterally inner double sheet portions 7a is adhered at an upper surface of the liquid permeable topsheet 3 that is provided at a side portion of the absorbent body 4 by a hot-melt adhesive or the like. A base edge portion of each of the laterally outer double sheet portions 7b is adhered to a side edge portion of the liquid impermeable backsheet 2 that laterally protrudes from the absorbent body 4 by a hot-melt adhesive or the like. With the above structure, the inner standing gathers 10 that stand toward the skin side are formed by the laterally inner double sheet portions 7a, and the outer standing gathers 11 that stand toward the skin side are formed by the laterally outer double sheet portions 7b, respectively. Here, as illustrated in FIG. 3, the threadlike elastic stretchable members 12 and 13 are not provided at both end portions of the side non-woven fabrics 7 in the longitudinal direction, and the laterally inner double sheet portions 7a are bonded at the absorbent body 4 side by the hot-melt adhesive or the like. Here, in this embodiment, the standing gathers BS may include at least the outer standing gathers 11 that constitute the side flaps.

(Absorbent Body Concave Portion 20)

An absorbent body concave portion 20 for flowing the urine therein is formed at a skin side surface of the absorbent body 4 (surface at a liquid permeable topsheet 3 side) along the longitudinal direction. The absorbent body concave portion 20 is provided to receive the expelled urine, while temporarily reserving the urine, promote diffusion of the urine in front and rear directions, and increase absorption rate of the urine into the absorbent body 4 to prevent side leak.

The absorbent body concave portion 20 is formed at the skin side surface of the absorbent body 4 like a concave groove or a slit along the longitudinal direction including the urine expelling area H. In the example of FIG. 2, the absorbent body concave portion 20 is formed at the skin side surface of the absorbent body 4 as a non-penetrating concave groove provided with a bottom surface that is concaved toward a non-skin side surface (surface at a liquid impermeable backsheet 2 side) with respect to its surrounding.

FIG. 1 illustrates an example in which the single absorbent body concave portion 20 is formed on a center line extending in the longitudinal direction at a center portion in a pad width direction corresponding to the urine expelling area H.

The absorbent body concave portion 20 may be formed by, for example, compression from the skin side surface of the absorbent body 4. Alternatively, as another example, the absorbent body concave portion 20 may be previously formed while fiber stacking the absorbent body 4 or the like, not by compression. By forming the absorbent body concave portion 20 not by compression, deformation of the absorbent body concave portion 20 due to pressure of legs can be prevented, and absorbency and diffusibility of the urine can be improved.

Figure 4A:
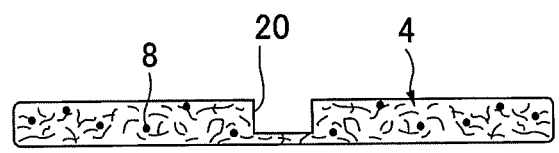
FIG. 4A is a cross-sectional view illustrating an example of a structure of an absorbent body.
Figure 4B:
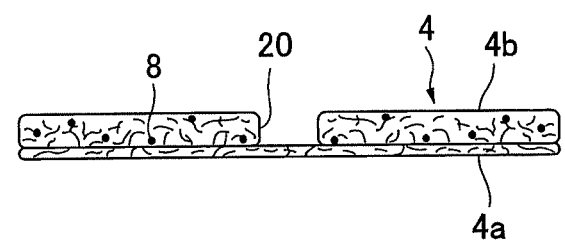
FIG. 4B is a cross-sectional view illustrating an example of a structure of the absorbent body.

FIG. 4A and FIG. 4B are cross-sectional views each illustrating an example of a structure in which the absorbent body concave portion 20 is formed not by compression. FIG. 4A illustrates a structure in which the absorbent body concave portion 20 is formed while fiber stacking. FIG. 4B illustrates a structure in which the absorbent body concave portion 20 is formed by a stacked structure or the like of a lower layer absorbent body 4a and one or a plurality of (one in the illustrated example) upper layer absorbent bodies 4b in which a n opening corresponding to the absorbent body concave portion 20 is formed. The absorbent body concave portion 20 may be formed as a slit that penetrates the skin side surface to the non-skin side surface of the absorbent body 4 in the thickness direction where the pulp and the polymer that constitute the absorbent body 4 do not exist.

The depth of the absorbent body concave portion 20 may be greater than or equal to the thickness of the absorbent body 4, specifically, approximately 5 to 20 mm. The depth of the absorbent body concave portion 20 is not necessarily constant, and may be varied in the longitudinal direction or in the width direction. For example, when varying the depth in the longitudinal direction, the depth may be relatively deeper at a portion corresponding to the urine expelling area H, while the depth becomes relatively shallower as reaching the both end portions of the absorbent body concave portion 20. Further, the absorbent body concave portion 20 may be formed in an opposite relationship from this. Further, when varying the depth in the width direction, as described above with reference to FIG. 4B, for example, the lower layer absorbent body 4a and two layers of the upper layer absorbent bodies 4b in which penetrating grooves are respectively formed may be included, while the width of the groove of the upper layer may be formed to be larger than that of the lower layer of the two upper layer absorbent bodies 4b. With this, the absorbent body concave portion 20 whose depth becomes stepwisely shallower from the center in the width direction toward both sides can be formed.

Further, as illustrated in FIG. 1 and FIG. 2, an emboss portion 21 may be provided in the absorbent body concave portion 20 along the absorbent body concave portion 20. The emboss portion 21 may be formed by embossing from the skin side surface of the liquid permeable topsheet 3 under a state that the liquid permeable topsheet 3 is stacked on the skin side surface of the absorbent body 4. With this, the liquid permeable topsheet 3 can be placed along inner surfaces of the absorbent body concave portion 20. By placing the liquid permeable topsheet 3 along the inner surfaces of the absorbent body concave portion 20 while providing the emboss portion 21 at the bottom surface of the absorbent body concave portion 20, deformation of the absorbent body concave portion 20 due to pressure of legs from inner sides at groins of the legs when being worn can be prevented, and the shape of the absorbent body concave portion 20 can be retained. Further, urine current along the absorbent body concave portion 20 can be easily generated.

The emboss portion 21 may be formed over the entire length of the absorbent body concave portion 20, however, as the illustrated example, if it is impossible to provide the emboss portion 21 at an end portion of a zone of a gradually decreasing width 23, the emboss portion 21 may not be provided at such a portion. It is preferable that the emboss portion 21 is constituted by a first emboss 21a having a wavy shape along the longitudinal direction of the absorbent body concave portion 20, and second embosses 21b that are formed along the concave groove at side edge portions opposite of concave portions of the first emboss 21a that are protruding outward in the width direction. With this, strength against pressure of legs from both lateral sides toward inside can be increased, and the absorbent body concave portion 20 is furthermore hardly deformed. When providing the emboss portion 21, it is preferable that polymer is not provided in an absorbent body portion at the bottom portion of the absorbent body concave portion 20.

However, as another example, without providing the emboss portion 21, a space of the absorbent body concave portion 20 may be formed at the non-skin side of the liquid permeable topsheet 3 by stacking the liquid permeable topsheet 3 as an upper layer on the absorbent body 4.

It is preferable to from the absorbent body 4 such that the density of the bottom surface of the absorbent body concave portion 20, and the density of its surrounding (portion other than the absorbent body concave portion 20) are approximately equal under a state that the emboss portion 21 is not formed. In other words, it is preferable that the above described densities of the absorbent body to be approximately equal by forming the absorbent body concave portion 20 to be a concave groove by the above described fiber stacking, two layered structure or the like, not by compression. With this, diffusibility of the urine in the absorbent body 4 is improved.

The fabric weight per unit area of the pulp of the portion of the absorbent body 4 at the bottom portion of the absorbent body concave portion 20 (portion at the liquid impermeable backsheet 2 side, non-skin side portion) may be 0 g/m$^2$ to 210 g/m$^2$, and preferably, 70 g/m$^2$ to 190 g/m$^2$. It is preferable that a predetermined fabric weight per unit area of the absorbent polymer 8 is dispersedly mixed at this portion of the absorbent body 4, however, if the emboss portion 21 is provided, it is possible not to provide the polymer at this portion.

Figure 5:
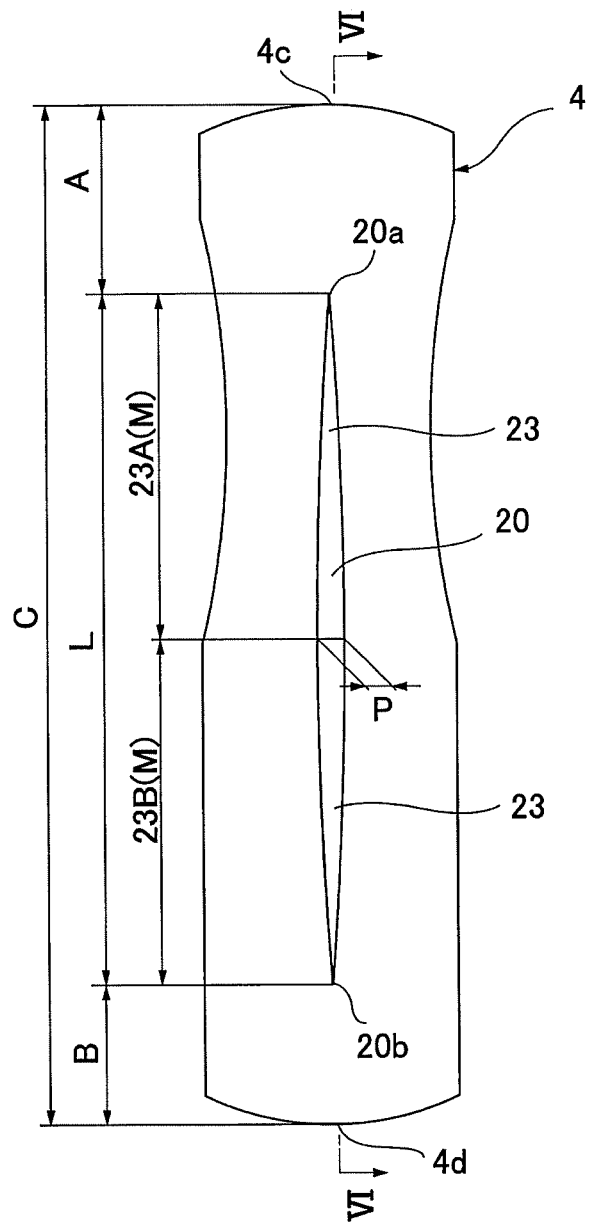
FIG. 5 is a plan view illustrating an example of a specific structure of an absorbent body concave portion of the embodiment.
Figure 6:
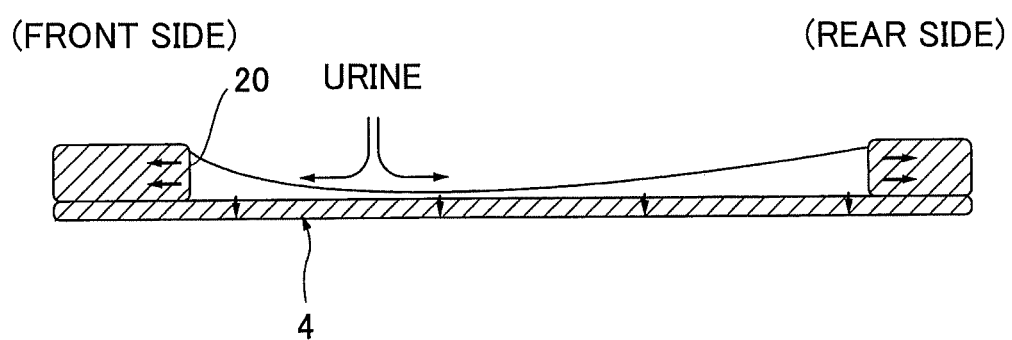
FIG. 6 is a cross-sectional view taken along line VI-VI of FIG. 5.
Figure 7A:
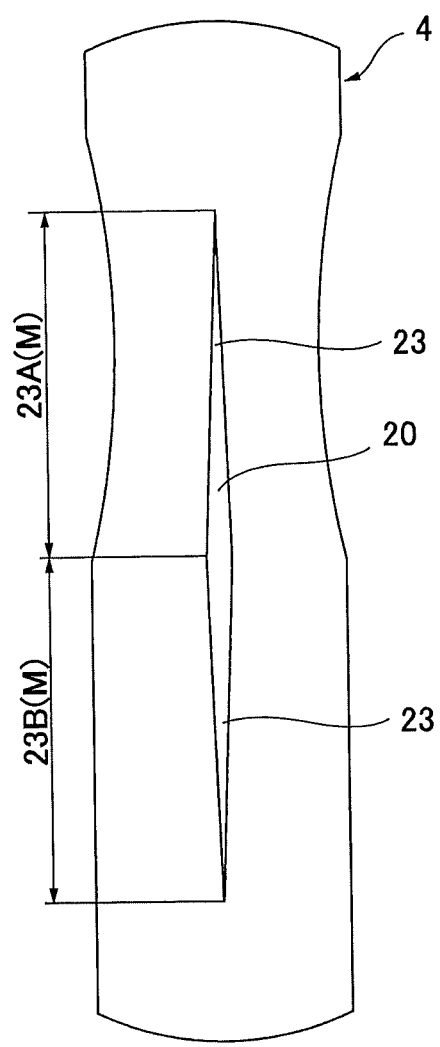
FIG. 7A is a plan view illustrating another example of a specific structure of the absorbent body concave portion of the embodiment.
Figure 7B:
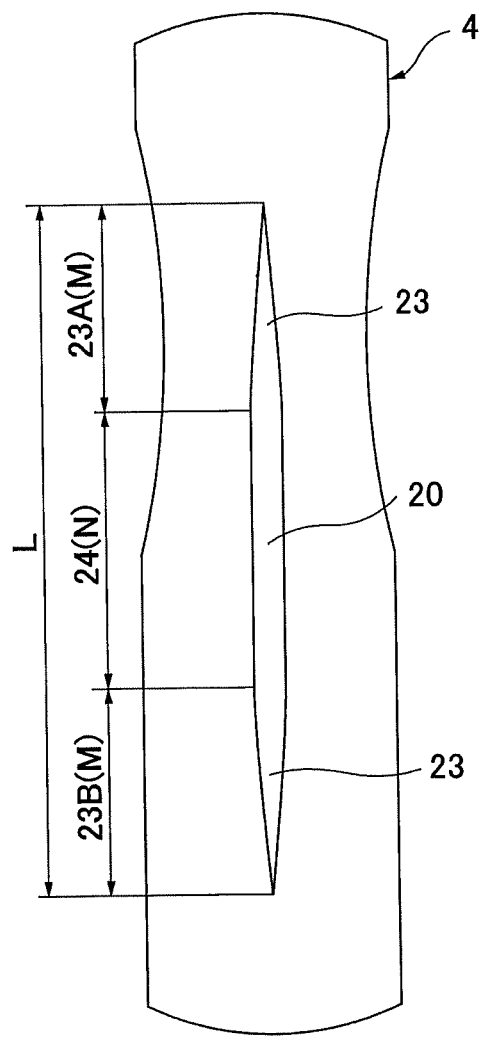
FIG. 7B is a plan view illustrating another example of a specific structure of the absorbent body concave portion of the embodiment.

FIG. 5, FIG. 7A and FIG. 7B are plan views each illustrating an example of a specific structure of the absorbent body concave portion 20 of the embodiment. FIG. 6 is a cross-sectional view taken along line VI-VI of FIG. 5.

In this embodiment, each of the longitudinal end portions of the absorbent body concave portion 20 is formed as the zone of a gradually decreasing width 23 having a tapered shape whose width is gradually decreased toward an end portion side, and each of the zones of a gradually decreasing width 23 is formed to have a length that is greater than or equal to 20% of the total length L of the absorbent body concave portion (zone length M of the zone of a gradually decreasing width 23 is M≥0.2 L). The zone of a gradually decreasing width 23 is a zone that is formed such that a distance (width) between both side walls gradually decreases toward the longitudinal end portion of the absorbent body concave portion 20. In the zone of a gradually decreasing width 23, a cross-sectional area of the absorbent body concave portion 20 gradually decreases toward the longitudinal end portion side. Here, the zone of a gradually decreasing width 23 that is provided at a front end portion in the longitudinal direction is referred to as a front-side zone of a gradually decreasing width 23A, and the zone of a gradually decreasing width 23 provided at a rear end portion in the longitudinal direction is referred to as a rear-side zone of a gradually decreasing width 23B. Each of the front-side zone of a gradually decreasing width 23A and the rear-side zone of a gradually decreasing width 23B is formed to have a length that is greater than or equal to 20% of the total length L of the absorbent body concave portion 20.

Next, an absorption mechanism of the urine at the absorbent body concave portion 20 is described.

The urine expelled to the urine expelling area H flows into the absorbent body concave portion 20. Next, while flowing along the absorbent body concave portion 20, the urine passes inner walls of the absorbent body concave portion 20 to be absorbed and retained in the absorbent body 4. At this time, if the absorbent body concave portion is formed to have the same width over the entire length as conventionally, the amount of the urine that flows in the absorbent body concave portion decreases and strength of urine current is decreased as moving toward both longitudinal end sides.

However, according to the incontinence pad 1 of the embodiment, as the zone of a gradually decreasing width 23 is provided at each of the both end portions of the absorbent body concave portion 20 for a predetermined length, lowering of the strength of the urine current can be suppressed. With this, the urine can flow to the end portion sides of the absorbent body concave portion 20, and the urine can diffuse to a wide range of the absorbent body 4 to be absorbed. Specifically, when assuming that the amount of the urine is the same, compared with a structure in which the width is equal, as the cross-sectional area of the flow path gradually decreases in the zone of a gradually decreasing width 23, the urine can flow to a longer range in the longitudinal direction of the flow path. Thus, in addition to suppressing lowering of the strength of the urine current, the urine can be diffused to a wide range of the absorbent body 4. Further, as illustrated in FIG. 6, as the flow path area of the urine gradually decreases toward the longitudinal end portion side in the zone of a gradually decreasing width 23, water level of the flowing urine gradually increases. Thus, contact area between the urine and both side surfaces of the absorbent body concave portion 20 in the height direction increases, and the amount of the urine that is drawn into the absorbent body 4 by capillary action increases. With this, the urine can be more easily absorbed in the absorbent body 4. Thus, the urine can flow to the front and rear end portions of the absorbent body concave portion 20, and the urine can be diffused over the entirety of the absorbent body 4.

Figure 9:
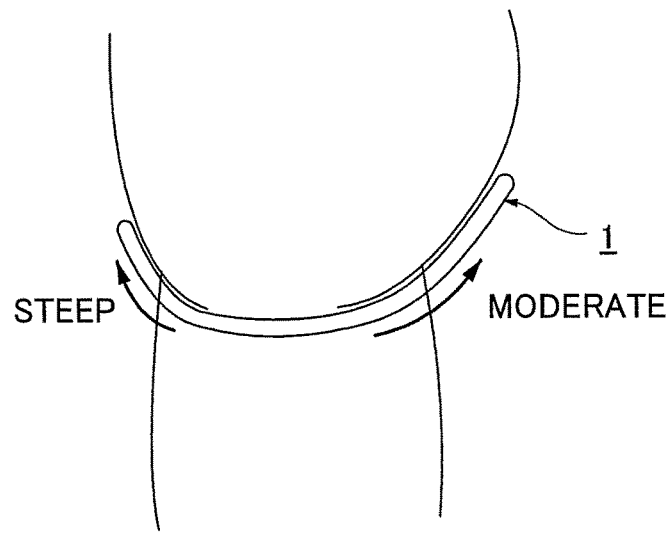
FIG. 9 is a cross-sectional view illustrating a human body wearing an incontinence pad.

FIG. 9 is a schematic view illustrating a state in which a wearer wears the incontinence pad 1. When the wearer wears the incontinence pad 1, front and rear ends of the incontinence pad 1 are curved upwardly along the curves of the human body in front and rear directions of the body. Thus, while a large amount of urine is intensively absorbed near the urine expelling area H, the urine may not diffuse to the front and rear end portions from the urine expelling area H, and not all of original absorption capacity of the absorbent body 4 is used. As a countermeasure for this problem, an amount of polymer may be increased at the urine expelling area H and its vicinity. However, if the containing ratio of the polymer is increased, so-called "gel blocking" may occur in which adjacent polymers that are swelled by absorbing water are bonded, and desired water absorbing power cannot be actualized after all. In this embodiment, as described above, the urine can flow to the long range of the flow path in the longitudinal direction. Thus, even when the front and rear ends are curved upwardly when the incontinence pad 1 is worn, the urine can easily flow to ends of the absorbent body concave portion 20, and the urine can contact a large range of the inner surfaces of the absorbent body concave portion 20 to be easily absorbed by the absorbent body 4. Thus, the urine can be diffused to the entirety of the absorbent body 4, and use of the original absorption capacity of the absorbent body 4 can be optimized.

In the example illustrated in FIG. 5 and FIG. 7A, the absorbent body concave portion 20 is formed to have tapered shapes in each of which the width is gradually decreased from a predetermined point in an intermediate portion in the longitudinal direction (hereinafter, referred to as a "longitudinal midpoint") toward the respective end. In other words, the front-side zone of a gradually decreasing width 23A and the rear-side zone of a gradually decreasing width 23B are directly connected in front and rear, and the front-side zone of a gradually decreasing width 23A is provided at a front side of the longitudinal midpoint, and the rear-side zone of a gradually decreasing width 23B is continuously connected from a rear end of the front-side zone of a gradually decreasing width 23A. With this structure, the urine can easily diffuse to the front and rear ends from the longitudinal midpoint. In the illustrated example, the longitudinal midpoint is set at a center point (center) of the absorbent body concave portion 20 in the longitudinal direction.

In such a case, as illustrated in FIG. 5, FIG. 7A and FIG. 7B, the front-side zone of a gradually decreasing width 23A and the rear-side zone of a gradually decreasing width 23B may be formed to have substantially the same zone length.

However, as another example, the longitudinal midpoint may be set at a position that is shifted toward a front side or a rear side in the longitudinal direction. In such a case, the front-side zone of a gradually decreasing width 23A and the rear-side zone of a gradually decreasing width 23B may have different zone lengths (not illustrated in the drawings). When the zone lengths are different, for example, the zone length of the rear-side zone of a gradually decreasing width 23B may be relatively longer than the zone length of the front-side zone of a gradually decreasing width 23A. This structure can correspond to a phenomenon that the amount of urine that flows toward the rear side is relatively larger than the amount of urine that flows toward the front side due to the structure of the human body.

An outline of the zone of a gradually decreasing width 23 from the midpoint toward each of both ends in the longitudinal direction may be an arc-shaped curved line that bulges outwardly or inwardly in the width direction or may be a linear line.

FIG. 5 illustrates an example of a case in which the outline of the zone of a gradually decreasing width 23 from the midpoint toward each of the both ends in the longitudinal direction is an arc-shape curved line that bulges outwardly in the width direction. In the example illustrated in FIG. 5, the outlines of the zone of a gradually decreasing width 23 at both sides are formed by arc-shape curved lines extending at both sides of a center line extending in the longitudinal direction (corresponding to line VI-VI, hereinafter, simply referred to as a "longitudinally extending center line") from the center point in the longitudinal direction to the both ends and each bulging outwardly in the width direction. Further, the outlines at both sides are connected on the longitudinally extending center line at each of the both ends in the longitudinal direction. In other words, an intersection of the outlines at the both ends is provided on the longitudinally extending center line. With this, the front-side zone of a gradually decreasing width 23A and the rear-side zone of a gradually decreasing width 23B are formed in a substantially eye shape as a whole.

As such, by forming the absorbent body concave portion 20 in the substantially eye shape, as the area of the sidewalls of the absorbent body concave portion 20 increases, the contact area between the urine and the absorbent body 4 increases, and the absorption amount can be increased. Further, as the width of the absorbent body concave portion 20 smoothly varies over the entirety in the longitudinal direction, the urine can smoothly flow along the absorbent body concave portion 20.

FIG. 7A illustrates an example of a case in which the outline of the zone of a gradually decreasing width 23 from the midpoint toward each of the both ends in the longitudinal direction is a linear line. In the example illustrated in FIG. 7A, the outlines of the zone of a gradually decreasing width 23 at both sides are formed by linear lines extending at the both sides of the longitudinally extending center line from the center point in the longitudinal direction to the both ends. Further, the outlines at both sides are connected on the longitudinally extending center line at each of the both ends in the longitudinal direction. In other words, an intersection of the outlines at the both ends is provided on the longitudinally extending center line. With this, the front-side zone of a gradually decreasing width 23A and the rear-side zone of a gradually decreasing width 23B are formed in a substantially rhombus shape as a whole.

In the example illustrated in FIG. 7B, in the absorbent body concave portion 20, an intermediate portion in the longitudinal direction is a fixed-width zone 24 whose width is uniform, and the front-side zone of a gradually decreasing width 23A and the rear-side zone of a gradually decreasing width 23B are continuously formed from both ends of the fixed-width zone 24, respectively. By providing such a fixed-width zone 24, the width of the absorbent body concave portion 20 can be retained at an appropriate size. With this, strength of urine current can be retained at both end portions in the longitudinal direction at which the strength of the urine current tend to be lowered, and the urine can be diffused to the end portion sides. Both side surfaces of the fixed-width zone 24 are formed by lines that are in parallel with each other.

In the example illustrated in FIG. 5, FIG. 7A and FIG. 7B, the outlines at both sides are connected on the longitudinally extending center line at each of the both ends of the absorbent body concave portion 20. However, as another example, both ends of the absorbent body concave portion 20 may be end surfaces respectively formed by linear lines that are perpendicular to the longitudinally extending center line, arc-shape curved lines that bulge outwardly in the longitudinal direction or the like.

Next, the size of the absorbent body concave portion 20 is described. With reference to FIG. 5, the planar size of the absorbent body concave portion 20 may be such that the length L in the pad longitudinal direction is 60 to 80% ($0.6\ C \leq L \leq 0.8\ C$) of the total length C of the absorbent body 4.

The maximum width P (the groove width of the bottom surface) of the absorbent body concave portion 20 may be 10 to 40 mm. Here, the absorbent body concave portion 20 may be formed such that wall surfaces at both sides are substantially perpendicular to a bottom surface of the absorbent body concave portion 20 so that the width at an opening side (upper side) and the width at the bottom surface side (lower side) in the depth direction are substantially equal.

Further, as described above, the zone length M of the zone of a gradually decreasing width 23 may be greater than or equal to 20% ($M \geq 0.2\ L$), preferably, 20 to 50% ($0.2\ L \leq M \leq 0.5\ L$), and more preferably, 30 to 50% ($0.3\ L \leq M \leq 0.5\ L$), of the total length L of the absorbent body concave portion 20. By setting the zone length M of the zone of a gradually decreasing width 23 to be greater than or equal to 20%, an effect of forming each of the end portions to be the tapered shape can be sufficiently obtained, and the urine can reach the zone of a gradually decreasing width 23 while retaining the strength of the urine current. In the example illustrated in FIG. 5 and FIG. 7A, the zone length M of the zone of a gradually decreasing width 23 is 50%.

Further, as illustrated in FIG. 7B, when the fixed-width zone 24 is formed at the intermediate portion of the absorbent body concave portion 20, the longitudinal size N of the fixed-width zone 24 may be 0 to 60% ($0 \leq N \leq 0.6$ L) of the total length L of the absorbent body concave portion 20. By setting the length of the fixed-width zone 24 to be less than or equal to 0.6 L, the urine can be diffused to the front-side zone of a gradually decreasing width 23A and the rear-side zone of a gradually decreasing width 23B without reducing the strength of the urine current even when the fixed-width zone 24 is provided.

In the planar view of FIG. 5, the absorbent body concave portion 20 is provided at an intermediate position of the absorbent body 4 with predetermined spaces at the front-side and the rear-side, respectively, in the longitudinal direction. The distance A between a front end 20a of the absorbent body concave portion 20 and a front end 4c of the absorbent body 4 in the pad longitudinal direction may be 10 to 25% ($0.15 \, C \leq A \leq 0.25 \, C$) of the total length C of the absorbent body 4, and a distance B between a rear end 20b of the absorbent body concave portion 20 and a rear end 4d of the absorbent body 4 in the pad longitudinal direction may be 10 to 20% ($0.1 \, C \leq B \leq 0.2 \, C$) of the total length C of the absorbent body 4. With this, an appropriate length of the absorbent body 4 can be provided at each of the front-side and the rear-side of the absorbent body concave portion 20, and certain areas of the absorbent body 4 at the end portion sides can be ensured for absorbing the body fluid flown to the front and rear ends of the absorbent body concave portion 20, respectively. With this, the body fluid absorbed in the absorbent body 4 from the absorbent body concave portion 20 can be more surely absorbed and retained in the absorbent body 4.

Further, as illustrated in FIG. 9, when the incontinence pad 1 is worn by a human body, as an upward curve is more moderate at the rear-side than the front-side, influence of the upward curve of the absorbent body 4 to cause suppression of urine current is smaller at the rear-side than the front-side, and the urine relatively easily flows toward the rear-side. Thus, the body fluid expelling area H may be positioned within the front-side zone of a gradually decreasing width 23 in the incontinence pad 1 of the embodiment. In other words, as illustrated in FIG. 1, the body fluid expelling area H may be positioned at an intermediate position of the front-side zone of a gradually decreasing width 23 with respect to the absorbent body concave portion 20. With this, urine current can be easily generated at the front-side at which the urine relatively hardly flows.

Figure 8A:
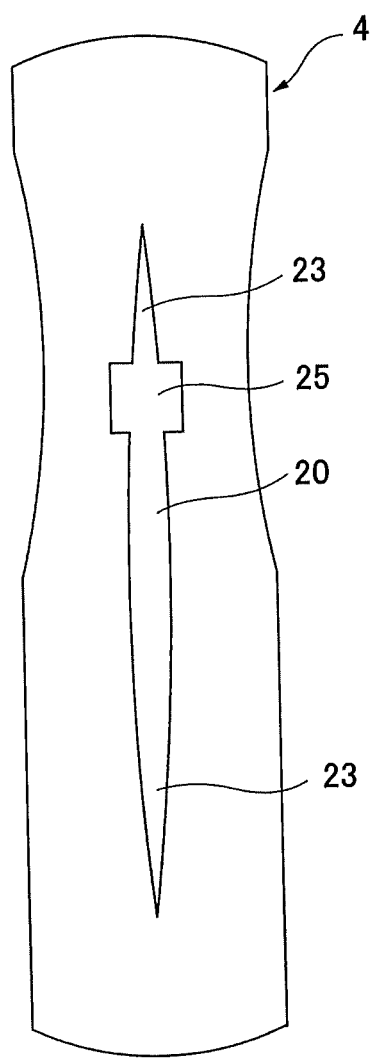
FIG. 8A is a plan view illustrating another example of a specific structure of the absorbent body concave portion of the embodiment.
Figure 8B:
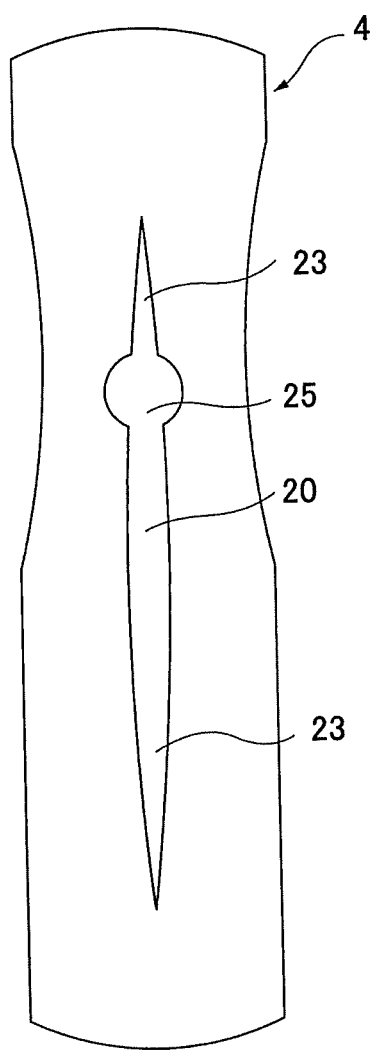
FIG. 8B is a plan view illustrating another example of a specific structure of the absorbent body concave portion of the embodiment.

FIG. 8A and FIG. 8B are plan views each illustrating another example of a specific structure of the absorbent body concave portion 20 of the embodiment.

In the example illustrated in FIG. 8A and FIG. 8B, the incontinence pad 1 may include a fluid trapping portion 25 having a wider width at a site in the absorbent body concave portion 20 corresponding to the urine expelling area H. The fluid trapping portion 25 is a reserving space for temporarily reserving the urine when the urine is expelled, and is formed to have a wider and substantially equal width at both sides of the absorbent body concave portion 20 at the site corresponding to the urine expelling area H and its vicinity. After the urine is temporarily reserved in the trapping portion 25, the urine flows along the absorbent body concave portion 20 in the front and rear directions. The planar shape of the fluid trapping portion 25 may be any of a rectangular shape (FIG. 8A), a polygonal shape and a rhombus shape, or any of a circular shape (FIG. 8B) and an elliptical shape that is longer in the pad longitudinal direction or in the width direction. The planar shape of the fluid trapping portion 25 may be, for example, an elliptical shape that is longer in the pad longitudinal direction. With this, reserving and diffusing of the urine can be smoothly performed.

Figure 10A:
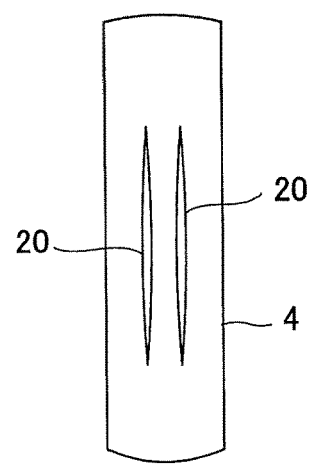
FIG. 10A is a plan view illustrating another example of the structure of the absorbent body concave portion of the embodiment.
Figure 10B:
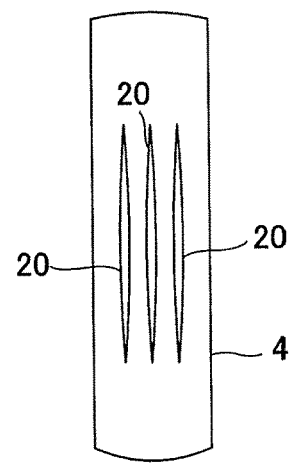
FIG. 10B is a plan view illustrating another example of the structure of the absorbent body concave portion of the embodiment.
Figure 10C:
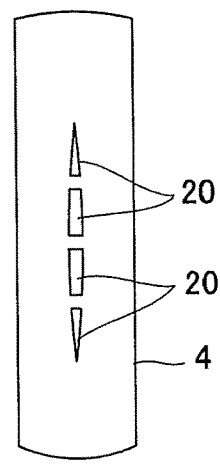

Further, the absorbent body concave portion 20 may be provided in various embodiments. FIG. 10A to FIG. 10C are plan views each illustrating another example of the structure of the absorbent body concave portion 20 of the embodiment.

In the example illustrated in FIG. 10A and FIG. 10B, a plurality of the absorbent body concave portions 20 are formed that are spaced apart from each other in the width direction of the incontinence pad 1. The number of the absorbent body concave portions 20 may be even as illustrated in FIG. 10A, or odd as illustrated in FIG. 10B. By forming the plurality of the absorbent body concave portions 20 as such, even when a large amount of the urine is expelled at once, the diffusion effect of the urine and the absorption efficiency of the urine can be furthermore improved.

Further, in the example illustrated in FIG. 10C, the absorbent body concave portion 20 is formed by discontinuity lines that are spaced apart from each other in the pad longitudinal direction. By forming the absorbent body concave portion 20 by the discontinuity lines, a portion where the absorbent body concave portion 20 is not formed functions as a reinforcing portion, and the absorbent body concave portion 20 is hardly deformed even when external force such as the pressure of legs is applied to the absorbent body concave portion 20 from both sides in the width direction. When the absorbent body concave portion 20 is formed by the discontinuity lines as such, it is preferable that the total of the length of the lines is 60 to 80% of the total length of the absorbent body 4.

In each of the structures illustrated in FIG. 10A to FIG. 10C, the absorbent body concave portion 20 may be formed at an area including a site corresponding to the urine expelling area H, and also formed like a line that is long in the pad longitudinal direction.

Further, the absorbent body concave portion 20 may have a structure in which one or a plurality of branched portions are provided. FIG. 11A to FIG. 11F are plan views each illustrating another example of the structure of the absorbent body concave portion 20 of the embodiment.

Figure 11A:
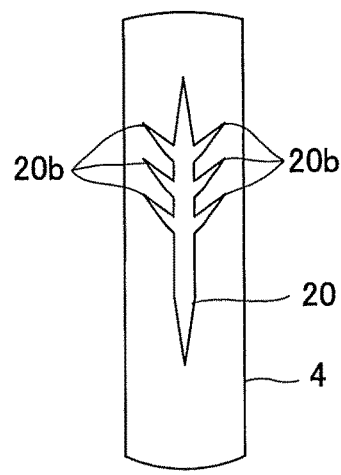
FIG. 11A is a plan view illustrating another example of the structure of the absorbent body concave portion of the embodiment.
Figure 11B:
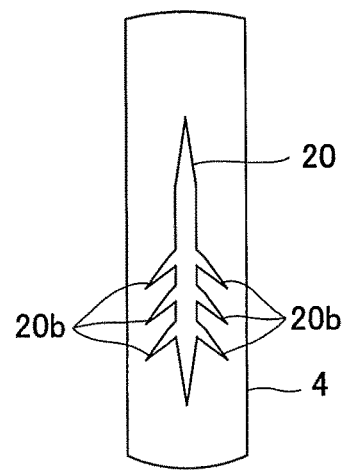
FIG. 11B is a plan view illustrating another example of the structure of the absorbent body concave portion of the embodiment.
Figure 11C:
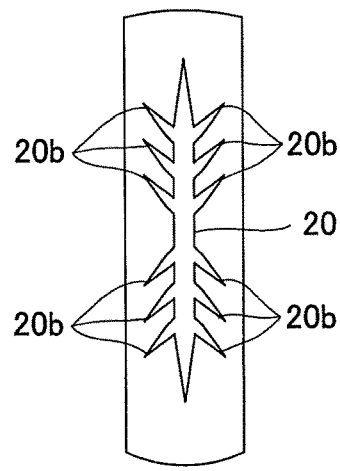
FIG. 11C is a plan view illustrating another example of the structure of the absorbent body concave portion of the embodiment.

In the example illustrated in FIG. 11A to FIG. 11C, the absorbent body concave portion 20 may have a structure in which branched portions 20b extending from both side edges to outsides, respectively, are provided. In FIG. 11A and FIG. 11B, a plurality of (three at each side in the illustrated example) the branched portions 20b that are extending from both side edges of the absorbent body concave portion 20 to outsides and inclined toward an end portion side in the pad longitudinal direction are provided at the front-side or the rear-side in the pad longitudinal direction. In FIG. 11C, a plurality of (three at each side in the illustrated example) branched portions 20b that are extending from both side edges of the absorbent body concave portion 20 to outsides and inclined toward an end portion side in the pad longitudinal direction are provided at each of the front-side and the rear-side in the pad longitudinal direction. By providing such branched portions 20b, the urine temporarily reserved in the absorbent body concave portion 20 can diffuse along the absorbent body concave portion 20 to a wide area of the absorbent body 4, and the urine can be absorbed in the wider area of the absorbent body 4.

Figure 11D:
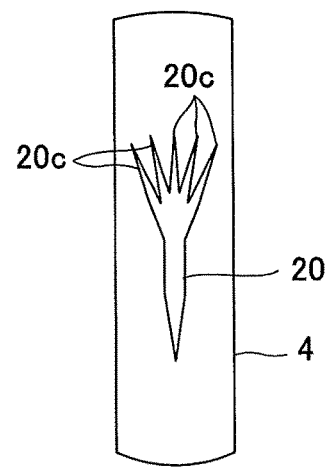
FIG. 11D is a plan view illustrating another example of the structure of the absorbent body concave portion of the embodiment.
Figure 11E:
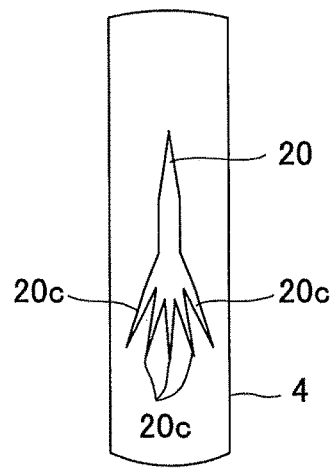
FIG. 11E is a plan view illustrating another example of the structure of the absorbent body concave portion of the embodiment.
Figure 11F:
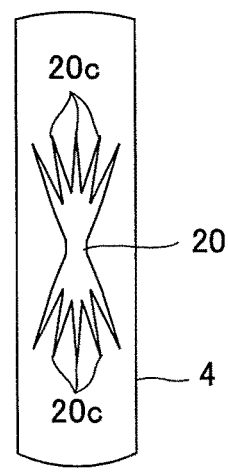
FIG. 11F is a plan view illustrating another example of the structure of the absorbent body concave portion of the embodiment.

Further, in the example illustrated in FIG. 11D to FIG. 11F, the absorbent body concave portion 20 may have a structure in which a plurality of branched portions 20c radially extending from an end in the longitudinal direction are provided. In FIG. 11D and FIG. 11E, the plurality of (five in the illustrated example) branched portions 20c that are radially branched from the absorbent body concave portion 20 are provided at the front end or the rear end in the pad longitudinal direction. In FIG. 11F, the plurality of (five in the illustrated example) branched portions 20c that are radially branched from the absorbent body concave portion 20 are provided at each of the front end and the rear end in the pad longitudinal direction. By providing such branched portions 20c, the urine temporarily reserved in the absorbent body concave portion 20 can diffuse along the absorbent body concave portion 20 to a wide area of the absorbent body 4, and the urine can be absorbed in the wider area of the absorbent body 4.

As described in detail, according to the embodiment, the urine can easily flow to the front and rear end portions of the absorbent body concave portion 20, and the urine can be diffused to the entirety of the absorbent body 4.

Although a preferred embodiment of the present invention has been specifically illustrated and described, it is to be understood that minor modifications may be made therein without departing from the spirit and scope of the invention as defined by the claims.

The present application is based on and claims the benefit of priority of Japanese Priority Application No. 2015-151811 filed on Jul. 31, 2015, the entire contents of which are hereby incorporated by reference.

NUMERALS

1 . . . incontinence pad, 2 . . . liquid impermeable backsheet, 3 . . . liquid permeable topsheet, 4 . . . absorbent body, 5 . . . encapsulating sheet, 7-side non-woven fabric, 8 . . . super absorbent polymer, 10 . . . inner standing gather, 11 . . . outer standing gather, 12, 13 . . . threadlike elastic stretchable member, 20 . . . absorbent body concave portion, 21 . . . emboss portion, 23 . . . zone of a gradually decreasing width, 24 . . . fixed-width zone, 25 . . . fluid trapping portion

What is claimed is:

1. An absorbent article in which an absorbent body is provided between a liquid permeable topsheet and a backsheet, comprising:
an absorbent body concave portion provided at a liquid permeable topsheet side of the absorbent body along a longitudinal direction of the absorbent article at an area including a urine expelling site, said absorbent body concave portion having a depth that becomes a deepest at a portion corresponding to the urine expelling site and becomes a shallowest: at both end portions of the absorbent body concave portion,
both end portions of the absorbent body concave portion in the longitudinal direction respectively being zones of a gradually decreasing width, each having a tapered shape whose width is gradually decreased toward an end portion side, each of the zones of a gradually decreasing width being formed to have a length that is greater than or equal to 20% of the total length of the absorbent body concave portion,
wherein the absorbent body concave portion includes two tapered shapes whose widths are gradually decreased from a predetermined point in an intermediate portion in the longitudinal direction toward both ends, respectively, and a fluid trapping, portion provided so as to divide one of the two tapered shapes at a site corresponding to the urine expelling site, said fluid trapping portion having a width that is a greatest throughout the one of the two tapered shapes.

2. The absorbent article according to claim 1, wherein in the absorbent body concave portion, an intermediate portion in the longitudinal direction is a fixed-width zone whose width is uniform, and the zones of a gradually decreasing width are continuously formed at both ends of the fixed width zone.

3. The absorbent article according to claim 1, wherein the zones of a gradually decreasing width are formed such that a rear-side zone of a gradually decreasing width is formed relatively longer than a front-side zone of a gradually decreasing width.

4. The absorbent article according to claim 1, wherein a distance between a front end of the absorbent body concave portion and a front end of the absorbent body is formed to be a length that is 10 to 25% of the total length of the absorbent body, and a distance between a rear end of the absorbent body concave portion and a rear end of the absorbent body is formed to be a length that is 10 to 20% of the total length of the absorbent body.

5. The absorbent article according to claim 1, further comprising an emboss portion provided in the absorbent body concave portion along the absorbent body concave portion by embossing from a front surface side of the liquid permeable topsheet.

6. The absorbent article according to claim 1, wherein the absorbent body concave portion is formed at a center in a width direction of the absorbent article along the longitudinal direction.

7. The absorbent article according to claim 1, wherein a plurality of the absorbent body concave portions that are spaced apart from each other in a width direction of the absorbent article are formed along the longitudinal direction.

8. The absorbent article according to claim 1, wherein the absorbent body concave portion is formed by discontinuity lines that are spaced apart from each other in the longitudinal direction of the absorbent article.

9. The absorbent article according to claim 1, wherein in the absorbent body concave portion, branched portions each extending outwardly from both side edges, or branched portions radially extending from an end in the longitudinal direction are provided.

10. The absorbent article according to claim 1, wherein the depth of the absorbent body concave portion is equal or more than 50% of a thickness of the absorbent article.

11. The absorbent article according to claim 1, wherein the depth of the absorbent body concave portion is between 5 mm to 20 mm.

12. The absorbent article according to claim 1, wherein the fluid trapping portion is any of a rectangular shape, a polygonal shape and a rhombus shape, or any of a circular shape and an elliptical shape that is longer in the longitudinal direction or in a width direction of the absorbent article.

13. The absorbent article according to claim 1, wherein the absorbent body is formed by an upper layer and a lower layer, and only the upper layer has the absorbent body concave portion.

14. The absorbent article according to claim 13, wherein the upper layer has absorbent polymer and the lower layer does not have the absorbent polymer.

* * * * *